US009814409B2

(12) United States Patent
Wariar et al.

(10) Patent No.: US 9,814,409 B2
(45) Date of Patent: Nov. 14, 2017

(54) DETECTION OF CHRONIC OBSTRUCTIVE PULMONARY DISEASE EXACERBATIONS FROM BREATHING PATTERNS

(71) Applicant: Cardiac Pacemakers, Inc., St. Paul, MN (US)

(72) Inventors: Ramesh Wariar, Blaine, MN (US); Kenneth C. Beck, Liberty, UT (US); Yi Zhang, Plymouth, MN (US); Aiden Flanagan, Kilcolgan (IE); Bryan Allen Clark, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 411 days.

(21) Appl. No.: 14/538,312

(22) Filed: Nov. 11, 2014

(65) Prior Publication Data

US 2015/0148699 A1 May 28, 2015

Related U.S. Application Data

(60) Provisional application No. 61/908,790, filed on Nov. 26, 2013.

(51) Int. Cl.
*A61B 5/085* (2006.01)
*A61B 5/053* (2006.01)
(Continued)

(52) U.S. Cl.
CPC ............ *A61B 5/085* (2013.01); *A61B 5/0809* (2013.01); *A61B 5/053* (2013.01); *A61B 5/4839* (2013.01); *A61N 1/36* (2013.01)

(58) Field of Classification Search
CPC ....... A61B 5/053; A61B 5/0809; A61B 5/085; A61B 5/4839; A61N 1/36
(Continued)

(56) References Cited

U.S. PATENT DOCUMENTS 4,034,743 A * 7/1977 Greenwood ........... A61B 5/082
600/538
4,373,534 A * 2/1983 Watson ................ A61B 5/1135
600/534

(Continued)

FOREIGN PATENT DOCUMENTS

CN 105828710 A 8/2016
JP 2008000436 A 1/2008
(Continued)

OTHER PUBLICATIONS

Sund, Z.M., et al., "Remote daily real-time monitoring in patients with COPD—A feasibility study using a novel device", Respiratory Medicine, vol. 103, Issue 9, Sep. 2009, 1320-1328.
(Continued)

*Primary Examiner* — Navin Natnithithadha
(74) *Attorney, Agent, or Firm* — Schwegman Lundberg & Woessner, P.A.

(57) ABSTRACT

An apparatus may include a sensing circuit and a processor. The sensing circuit is configured to generate a sensed physiological signal, wherein the physiological signal includes respiration information of a subject. The processor includes an end expiratory volume (EEV) module configured to determine a value of EEV of the subject using the sensed physiological signal, and a lung hyperinflation detection module configured to generate an indication of lung hyperinflation of the subject according to the value of EEV and provide the indication to at least one of a user or process.

16 Claims, 4 Drawing Sheets

(51) Int. Cl.
*A61N 1/36* (2006.01)
*A61B 5/08* (2006.01)
*A61B 5/00* (2006.01)

(58) Field of Classification Search
USPC ........ 600/481, 483, 484, 529, 533, 536, 538
See application file for complete search history.

(56) References Cited

U.S. PATENT DOCUMENTS

| | | | | |
|---|---|---|---|---|
| 4,807,640 | A * | 2/1989 | Watson | A61B 5/1135 |
| | | | | 340/575 |
| 4,834,209 | A * | 5/1989 | Vogel | G01V 1/46 |
| | | | | 181/105 |
| 5,301,678 | A * | 4/1994 | Watson | A61B 5/4393 |
| | | | | 600/534 |
| 5,331,968 | A * | 7/1994 | Williams | A61B 5/0809 |
| | | | | 600/534 |
| 6,015,388 | A * | 1/2000 | Sackner | A61B 5/08 |
| | | | | 600/529 |
| 6,047,203 | A * | 4/2000 | Sackner | A41D 13/1281 |
| | | | | 600/301 |
| 6,076,015 | A | 6/2000 | Hartley et al. | |
| 6,341,504 | B1 * | 1/2002 | Istook | A61B 5/0002 |
| | | | | 2/69 |
| 6,413,225 | B1 * | 7/2002 | Sackner | A61B 5/0803 |
| | | | | 600/529 |
| 6,551,252 | B2 * | 4/2003 | Sackner | A61B 5/0205 |
| | | | | 600/301 |
| 7,267,652 | B2 * | 9/2007 | Coyle | A61B 5/0806 |
| | | | | 600/529 |
| 7,878,979 | B2 * | 2/2011 | Derchak | A61B 5/0806 |
| | | | | 600/529 |
| 8,249,686 | B2 | 8/2012 | Libbus et al. | |
| 8,285,356 | B2 | 10/2012 | Bly et al. | |
| 8,366,641 | B2 | 2/2013 | Wang et al. | |
| 8,417,325 | B2 | 4/2013 | Sachanandani et al. | |
| 8,628,480 | B2 * | 1/2014 | Derchak | A61B 5/0806 |
| | | | | 600/529 |
| 9,174,046 | B2 * | 11/2015 | Francois | A61B 5/6804 |
| 9,308,338 | B2 * | 4/2016 | Sinderby | A61B 5/091 |
| 2005/0119586 | A1 * | 6/2005 | Coyle | A61B 5/0806 |
| | | | | 600/538 |
| 2007/0049843 | A1 * | 3/2007 | Derchak | A61B 5/0806 |
| | | | | 600/538 |
| 2010/0275921 | A1 | 11/2010 | Schindhelm et al. | |
| 2011/0092795 | A1 * | 4/2011 | Derchak | A61B 5/0806 |
| | | | | 600/409 |
| 2012/0118290 | A1 * | 5/2012 | Sinderby | A61B 5/091 |
| | | | | 128/204.23 |
| 2014/0142652 | A1 * | 5/2014 | Francois | A61B 5/6804 |
| | | | | 607/42 |

FOREIGN PATENT DOCUMENTS

| | | |
|---|---|---|
| WO | WO-2012103216 A2 | 8/2012 |
| WO | WO-2015080860 A1 | 6/2015 |

OTHER PUBLICATIONS

"European Application Serial No. 14805441.4, Response filed Jan. 13, 2017 to Communication Pursuant to Rules 161(1) and 162 EPC dated Jul. 5, 2016", 10 pgs.

"International Application Serial No. PCT/US2014/065031, International Preliminary Report on Patentability dated Jun. 9, 2016", 13 pgs.

"International Application Serial No. PCT/US2014/065031, International Search Report dated Apr. 29, 2015", 6 pgs.

"International Application Serial No. PCT/US2014/065031, Invitation to Pay Additional Fees and Partial Search Report dated Feb. 11, 2015", 4 pgs.

"International Application Serial No. PCT/US2014/065031, Written Opinion dated Apr. 29, 2015", 11 pgs.

* cited by examiner

DETECTION OF CHRONIC OBSTRUCTIVE PULMONARY DISEASE EXACERBATIONS FROM BREATHING PATTERNS

CLAIM OF PRIORITY

This application claims the benefit of priority under 35 U.S.C. §119(e) of U.S. Provisional Patent Application Ser. No. 61/908,790, filed on Nov. 26, 2013, which is herein incorporated by reference in its entirety.

BACKGROUND

Chronic Obstructive Pulmonary Disease (COPD) is a progressive lung disease and includes chronic bronchitis, asthma, and emphysema. Chronic bronchitis is characterized by chronic cough with sputum production. Symptoms of chronic bronchitis such as airway inflammation, mucus hypersecretion, airway hyperresponsiveness, and eventual fibrosis of the airway walls may cause significant airflow and gas exchange limitations. Asthma is similar to chronic bronchitis, though the underlying cause is often an inherent defect of airway smooth muscle or the inflammatory milieu, which makes airway smooth muscle hyper-reactive. Similar to chronic bronchitis, chronic asthma can have similar airway wall thickening, leading to permanent and irreversible airflow obstruction. Emphysema is characterized by the destruction of the lung parenchyma. This destruction of the lung parenchyma leads to a loss of elastic recoil and tethering which maintains airway patency. Unlike the larger airways, bronchioles are not supported by cartilage. This means the bronchioles have little intrinsic support and therefore are susceptible to collapse when loss of tethering occurs, particularly during exhalation.

An acute exacerbation of COPD (AECOPD) is defined by a sudden worsening of symptoms (e.g. increase in or onset of cough, wheeze, and sputum changes) that typically last from several days to a couple of weeks. AECOPD is typically triggered by a bacterial infection, viral infection, allergens, or pollutants that quickly manifest into one or more of airway inflammation, mucus hypersecretion, and bronchoconstriction, which can significantly restrict airways. AECOPD is associated with an increase in morbidity and mortality of COPD patients. Delay in medical treatment for AECOPD can increase the risk of hospitalization for the patient, while prompt medical treatment can prevent worsening conditions and prevent hospitalization. The present inventors have recognized a need for improved monitoring of respiratory function in patients with pulmonary conditions.

OVERVIEW

This document discusses systems, devices and methods for improved monitoring of respiratory function in patients or subjects with pulmonary conditions. An apparatus example can include a sensing circuit and a processor. The sensing circuit is configured to generate a sensed physiological signal, wherein the physiological signal includes respiration information of a subject. The processor includes an end expiratory volume (EEV) module configured to determine a value of EEV of the subject using the sensed physiological signal, and a lung hyperinflation detection module configured to generate an indication of lung hyperinflation of the subject according to the value of EEV and provide the indication to at least one of a user or process.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An ambulatory medical device may include one or more of the features, structures, methods, or combinations thereof described herein. For example, an ambulatory respiration monitor may be implemented to include one or more of the advantageous features or processes described below. It is intended that such a monitor, or other implantable, partially implantable, wearable, or other ambulatory device need not include all of the features described herein, but may be implemented to include selected features that provide for unique structures or functionality. Such a device may be implemented to provide a variety of diagnostic functions.

Patients with COPD experience expiratory flow limitation (EFL). EFL not only can lead to "static" lung hyperinflation at rest, but also to dynamic lung hyperinflation as a result of conditions that increase ventilation, such as exercise, anxiety, or hypoxemia. AECOPD is usually associated with worsening EFL, which in turn can result in dynamic lung hyperinflation that contributes to the symptom of worsening dyspnea. Lung hyperinflation relates to an increased volume of residual air in the lungs that causes the lungs to overinflate, and can lead to rapid shallow breathing by the patient or subject.

Figure 1:
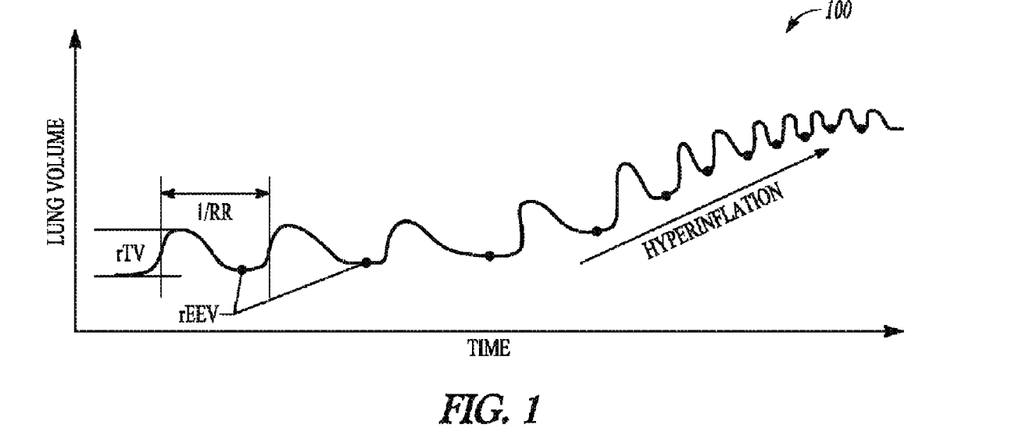
FIG. 1 shows an illustration of an example of a respiration waveform before and during an episode of lung hyperinflation.

FIG. 1 shows an illustration of an example of a respiration waveform before and during an episode of lung hyperinflation. The respiration waveform 100 may be included in a respiration signal. The vertical axis is representative of lung volume. The waveform can be obtained by sensing thoracic impedance of the patient. The peaks and valleys in the waveform 100 correspond to breathing cycles of a subject. Respiratory rate (RR) can be determined using the time between peaks, between valleys, or between other fiducial features in the waveform. Tidal volume (TV) can be determined using the difference in value between peaks and valleys in the waveform. End expiratory lung volume, or end expiratory volume (EEV), is the volume of residual air in the lungs of the subject at the end of the exhalation phase of respiration. A measure of EEV can be determined using the values of the valleys or negative peaks in the waveform (indicated by dots) in the Figure. Lung hyperinflation can be detected by monitoring EEV. In the waveform example of FIG. 1, EEV is shown increasing. Lung hyperinflation can be detected when the value of EEV exceeds a detection threshold value of lung hyperinflation.

An absolute measure of EEV is not necessary for detection of lung hyperinflation. This is because each patient can be used as his/her own control, so that lung hyperinflation can be detected using a relative increase in EEV from historical measures of EEV. Relative FEN (rEEV) maybe monitored using lung impedance, and lung hyperinflation can be detected when the change in rEEV exceeds a detection impedance value threshold. Other types of sensors can be useful in providing an indication of rEEV. Monitoring the motion or the change in dimensions of the chest of the subject, or monitoring respiration airflow of the subject may provide a surrogate measure of rEEV and may allow detection of lung hyperinflation.

Figure 2:
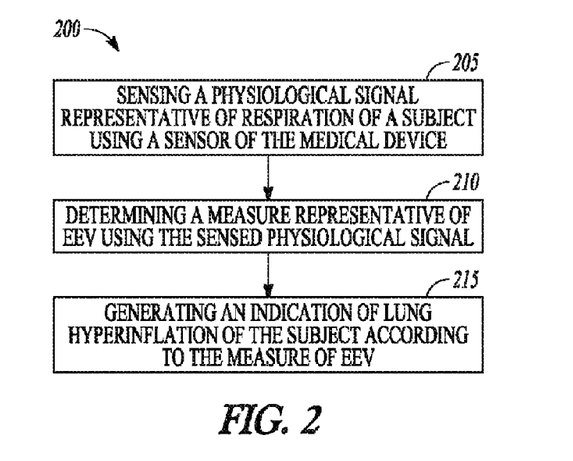
FIG. 2 shows an example of a method 200 of operating a medical device to detect lung hyperinflation.

FIG. 2 shows an example of a method of operating a medical device to detect lung hyperinflation. The medical device may be an ambulatory medical device. An ambulatory medical device may be implantable, partially implantable, or wearable and non-implantable.

At block 205, a physiological signal is sensed using a sensing circuit of the medical device. The physiological signal includes respiration information of the subject. The physiological signal may be generated using a respiration sensor, or the physiological signal may be generated using a sensing circuit that provides surrogate information of respiration of the subject. For example, the sensing circuit may generate an electrical signal representative of movement of the chest cavity of the subject to provide surrogate information concerning the subject's respiration. Examples of a surrogate sensor for sensing respiration are provided elsewhere herein.

At block 210, a value of end expiratory volume (EEV) of a subject is determined using the sensed physiological signal. EEV can be estimated directly using a thoracic impedance signal. Values of impedance can be calibrated to lung volume of the subject. A value of EEV can be estimated directly from a value of thoracic impedance using an impedance-to-lung volume conversion factor. EEV can be estimated using less direct methods using the surrogate information. For instance an accelerometer may be used to sense motion of the subject's chest cavity. The motion of the chest cavity can be calibrated to indicate lung volume of the subject. A value of EEV can be estimated using the detected motion of the chest cavity.

At block 215, an indication of lung hyperinflation of the subject is generated using the medical device according to the value of EEV. The indication may be provided to at least one of a user or process.

Figure 3:
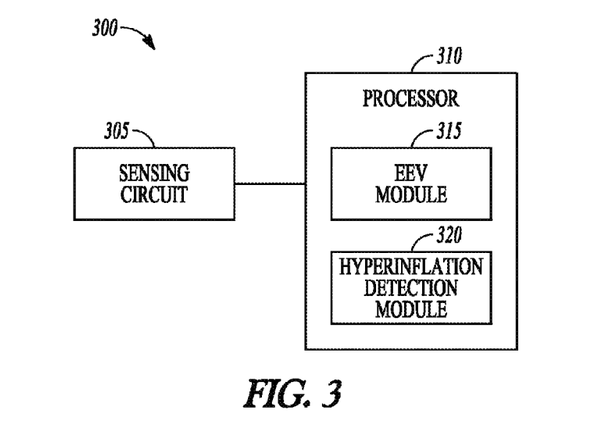
FIG. 3 shows a block diagram of portions of an example of a medical device to detect lung hyperinflation.

FIG. 3 shows a block diagram of portions of an example of a medical device 300 to detect lung hyperinflation. The device may be an ambulatory medical device that can be implantable, partially, implantable, or wearable. The device includes a sensing circuit 305 and a processor 310. The sensing circuit 305 generates a sensed physiological signal that includes respiration information.

The processor 310 may be a microprocessor, a digital signal processor, application specific integrated circuit (ASIC), or other type of processor, interpreting or executing instructions in software modules or firmware modules. The modules may include software, firmware, hardware circuits or any combination of software, firmware, and hardware. Multiple functions can be performed in one or more of the modules as desired. The sensing circuit 305 and the processor 310 can be in electrical communication such that signals can be communicated between the sensing circuit and processor even though there may be intervening circuitry.

The processor 310 includes an end expiratory volume (EEV) module 315 that determines a value of EEV of the subject using the sensed physiological signal, and a lung hyperinflation detection module 320. The lung hyperinflation detection module 320 generates an indication of lung hyperinflation of the subject according to the value of EEV and provides the indication to at least one of a user or process.

In some examples, the sensing circuit 305 includes a thoracic impedance sensing circuit. To measure thoracic impedance, electrodes may be placed across at least a portion of the thorax region of the subject to generate a sensed thoracic impedance signal that varies with breathing of the subject. In certain examples, the electrodes and the thoracic impedance sensing circuit are implantable. For instance, the electrodes may be implantable subcutaneously, implantable in the chest cavity, the bronchi, or implantable in the lung parenchyma or lung pleural space for example. An approach to measuring thoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference in its entirety. Some examples of such an implantable device include a device that provides electrical stimulation therapy (e.g., a pacemaker or implantable cardioverter/defibrillator) or provide a drug therapy (e.g., a drug pump), or the device may be incorporated into a bronchial valve.

The sensed thoracic impedance may be calibrated (e.g., by a clinician or automatically calibrated using an external device such as a continuous positive airway pressure or CPAP machine) to the breathing of the subject so that a measured value of thoracic impedance corresponds to a lung volume for the subject. The EEV module 315 can determine the value of EEV using the thoracic impedance signal. For instance, if the waveform example of FIG. 1 is representative of thoracic impedance, the valley of the waveforms provides a measure of thoracic impedance at EEV. The example shows that the value of thoracic impedance continues to increase; indicating that EEV is increasing. The lung hyperinflation detection module 320 may generate an indication of lung hyperinflation when the value of the thoracic impedance in the valleys of the waveform exceeds a specified (e.g., programmed) impedance threshold value for detection of lung hyperinflation. In certain examples, the lung hyperinflation module 320 may generate an indication of lung hyperinflation when the thoracic impedance in the valleys of the waveform remains above the lung hyperinflation detection threshold for a specified time duration.

In some examples, the EEV module 315 determines a central tendency of the thoracic impedance signal (e.g., a mean or median impedance signal). This may remove the tidal volume information from the thoracic impedance signal in order to simplify the determination of changes in EEV. The values of thoracic impedance may include a slow signal drift due to non-respiration sources. For example, the detection of lung hyperinflation may be complicated by increasing lung fluid associated with a heart failure condition (HF) of the subject.

Lung hyperinflation typically occurs over a time period of minutes to hours, while thoracic impedance changes due to HF typically occur over a time period of days to weeks. To distinguish changes in thoracic impedance due to lung hyperinflation from changes in thoracic impedance due to HF, the EEV module may determine a baseline thoracic impedance signal. The baseline may be updated regularly, such as every hour or every several hours, to remove the thoracic impedance changes due to HF. The lung hyperinflation module 320 may generate an indication of lung hyperinflation when the EEV changes to the detection threshold value within a specified time period (e.g., when the change occurs within minutes or hours rather than days). Thus, the lung hyperinflation detection module 320 may filter measurements of EEV to remove a change in the measurement of EEV contributed by the sensing circuit due to the fluid accumulation and preserve a change in the measurement EEV due to lung hyperinflation. Once separated from EEV, fluid accumulation could be used in combination with EEV to identify concomitant exacerbations of COPD along with exacerbation of other conditions such as HF.

The medical device may be an external device such as an external monitoring patch, a holter monitor, or a medical device incorporated into an article of clothing such as a vest. The device may be a percutaneously implantable device. For instance, the device may partially penetrate the skin, and be used for a short-term trial period. Such a percutaneous implant may be a diagnostic device or a bridge to a permanently implanted device. The device may be a therapeutic device that provides cardiac therapy, pulmonary therapy, or other therapies. The sensing circuit 305 may include an external impedance sensing circuit that uses electrodes in contact with the subject's skin to monitor thoracic impedance.

The sensing circuit 305 may generate a different physiological signal than a thoracic impedance signal. For instance, the sensing circuit 305 may generate a physiological signal that varies with motion of the thoracic cavity that indicates the breathing cycle of the subject. An example of a sensing circuit to detect breathing motion is a displacement sensing circuit. The displacement sensing circuit may provide an electrical signal that varies with the position or movement of the chest of the subject. A non-limiting example of a displacement sensing circuit is a strain gauge or strain sensor. Movement of the chest cavity or distention of one or more airways may cause a force or strain on the strain sensor that produces an electrical signal that varies with breathing of the patient. Other examples of the displacement sensing circuit may detect chest displacement through a change in capacitance or a change in magnetic field. The EEV module 315 may determine TV or RR using the physiological signal from the displacement sensing circuit and estimate a value of EEV using one or both of TV and RR. In another example, chest motion is detected using an acceleration sensing circuit (e.g., an accelerometer) that provides an acceleration signal representative of motion of the thoracic cavity.

In some examples, the sensing circuit 305 includes an airflow sensor to estimate EEV. In some examples, the sensing circuit 305 includes a pressure sensor that generates a physiological signal that includes information of pressure within the thoracic cavity of the subject. The EEV module 315 estimates EEV using a measure of thoracic pressure at end expiration. The lung hyperinflation detection module 320 may generate an indication of lung hyperinflation when the value of the thoracic pressure exceeds a specified threshold pressure value for detection of lung hyperinflation.

In some examples, the sensing circuit 305 includes a chemical sensor. Lung hyperinflation may result in poorer gas-blood exchange. The chemical sensor may provide an indication of one or more of pH, oxygen ($O_2$), and carbon dioxide ($CO_2$) levels in one or more of expired air, blood and tissue. The EEV module 315 may determine a measure of one or more of the levels to monitor the efficiency with which the body achieves blood-gas exchange. The lung hyperinflation module 320 may generate the indication of lung hyperinflation when the measured level of pH, $O_2$, or $CO_2$ changes relative to a threshold detection level value.

In some examples, the sensing circuit 305 provides multiple physiological signals. In certain examples, the EEV module 315 may use a first physiological signal to determine the end or other fiducial feature of the respiration cycle and a second physiological sensor to measure a value of EEV. For instance, the sensing circuit 305 may include both an acceleration sensing circuit and a thoracic impedance sensing circuit. The EEV module may initiate a measure of EEV using the thoracic impedance signal when the acceleration signal indicates the end of the respiration cycle. This may minimize or exclude noise sources from the impedance signal such as talking, coughing, sighing, etc., and may be useful to distinguish changes in thoracic impedance due to lung hyperinflation from changes in thoracic impedance due to HF. In another example, the EEV module 315 may initiate a measurement with a chemical sensor when the acceleration signal indicates the end of the respiration cycle.

In another example, the sensing circuit 305 may generate multiple physiological sensors, but one of the sensors may be corruptible due to certain patient conditions. For instance, physical activity of the patient may make it difficult to determine EEV using an accelerometer or a strain sensor. Physical activity may be indicated by the accelerometer or may be detected from an elevated heart rate sensed with a cardiac signal sensing circuit. The EEV module 315 may change from determining EEV using a first physiological signal (e.g., a force signal) to determining EEV using a second physiological signal (e.g., an impedance signal or a signal from a chemical sensor) when sensed physical activity of the subject exceeds a specified physical activity threshold. In another example, the EEV module 315 may change from determining EEV using a thoracic impedance signal to a different physiological signal when worsening HF of the subject is detected according to a different sensor or set of sensors.

In some examples, the medical device 300 includes two types of sensing circuits. The first type of sensing circuit estimates EEV relatively directly, such as by measuring chest displacement or thoracic impedance. The second type of sensing circuit estimates EEV more indirectly than the first type of sensing circuit, such as by monitoring an electrocardiogram or measuring thoracic pressure. This less direct type of sensing circuit may provide surrogate information of respiration of the subject. The EEV module 315 may change from determining values of EEV using the first type of sensing circuit to determining values of EEV using the second type of sensing circuit according to device-detected patient conditions. In certain examples, the EEV module 315 may use the second type of sensing circuit to trigger a determination of the measure of EEV using the first type of sensing circuit. For instance, the EEV module 315 may determine a measure of EEV using a thoracic impedance signal when both the thoracic respiration signal and the second physiological sensor signal indicate respiratory activity.

Figure 4:
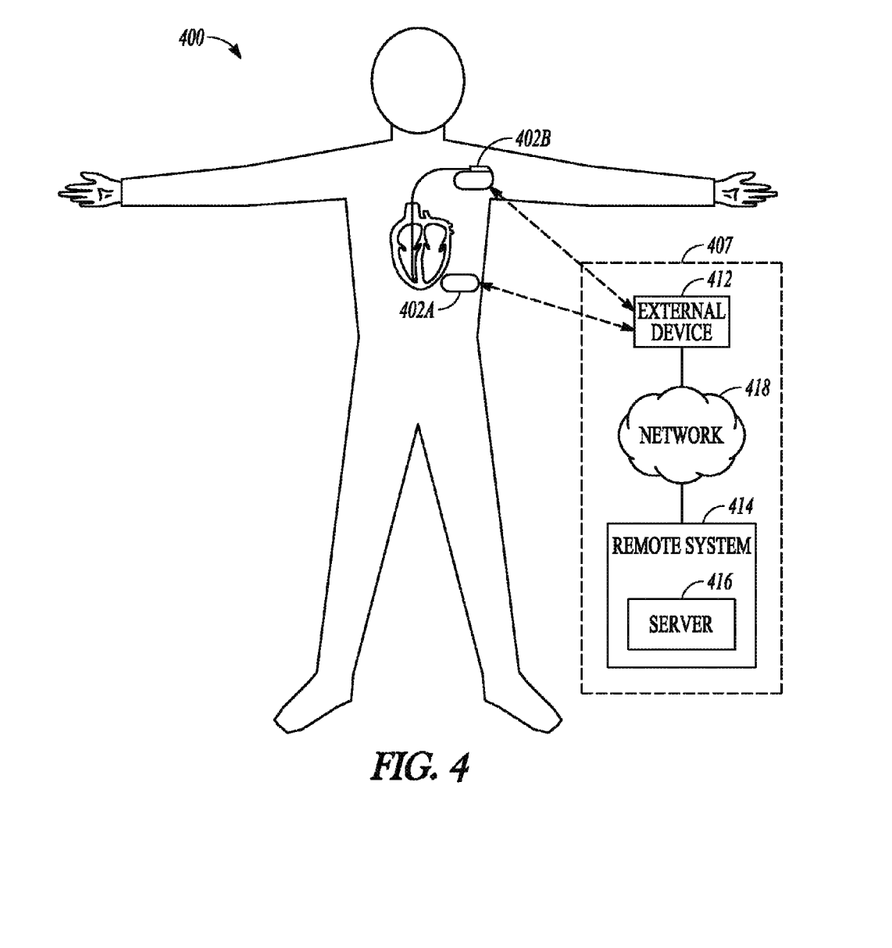
FIG. 4 shows a block diagram of portions of an example of a medical device system to detect lung hyperinflation.

FIG. 4 shows a block diagram of portions of an example of a medical device system 400 to detect lung hyperinflation. The system 400 includes an ambulatory medical device. The ambulatory medical device can be a wearable device 402A, such as a patch that monitors one or more physiological parameters of the subject for example. The wearable device may be incorporated into an article of clothing or may be adherable to the subject's skin. The ambulatory medical device can be an implantable device 402B, such as a pacemaker or implantable cardioverter/defibrillator (ICD) that provides electrical therapy such as heart chamber resynchronization therapy to the subject, or the implantable device can include a drug reservoir to provide a drug therapy to the subject. The implantable device includes one or more sensing circuits to monitor one or more physiological parameters of the subject and may be a diagnostic only device or a therapeutic device.

The medical device system 400 can include an external communication device 412 to communicate with the ambulatory medical device. The communication may be wireless using wireless telemetry. The external communication device 412 may communicate with a remote system 414 via a network 418 (e.g., the internet, a proprietary computer network, or a cellular phone network). The remote system 414 may include a server 416 remotely located from the external communication device 412 and the subject to perform patient management functions, such as accessing electronic medical records for example. The external communication device 412 may include a programmer to program therapy parameters of a device-based therapy provided by the ambulatory medical device. In certain examples, the external communication device 412 includes a repeater to communicate programming changes or other communication initiated by the remote system 414.

Figure 5:
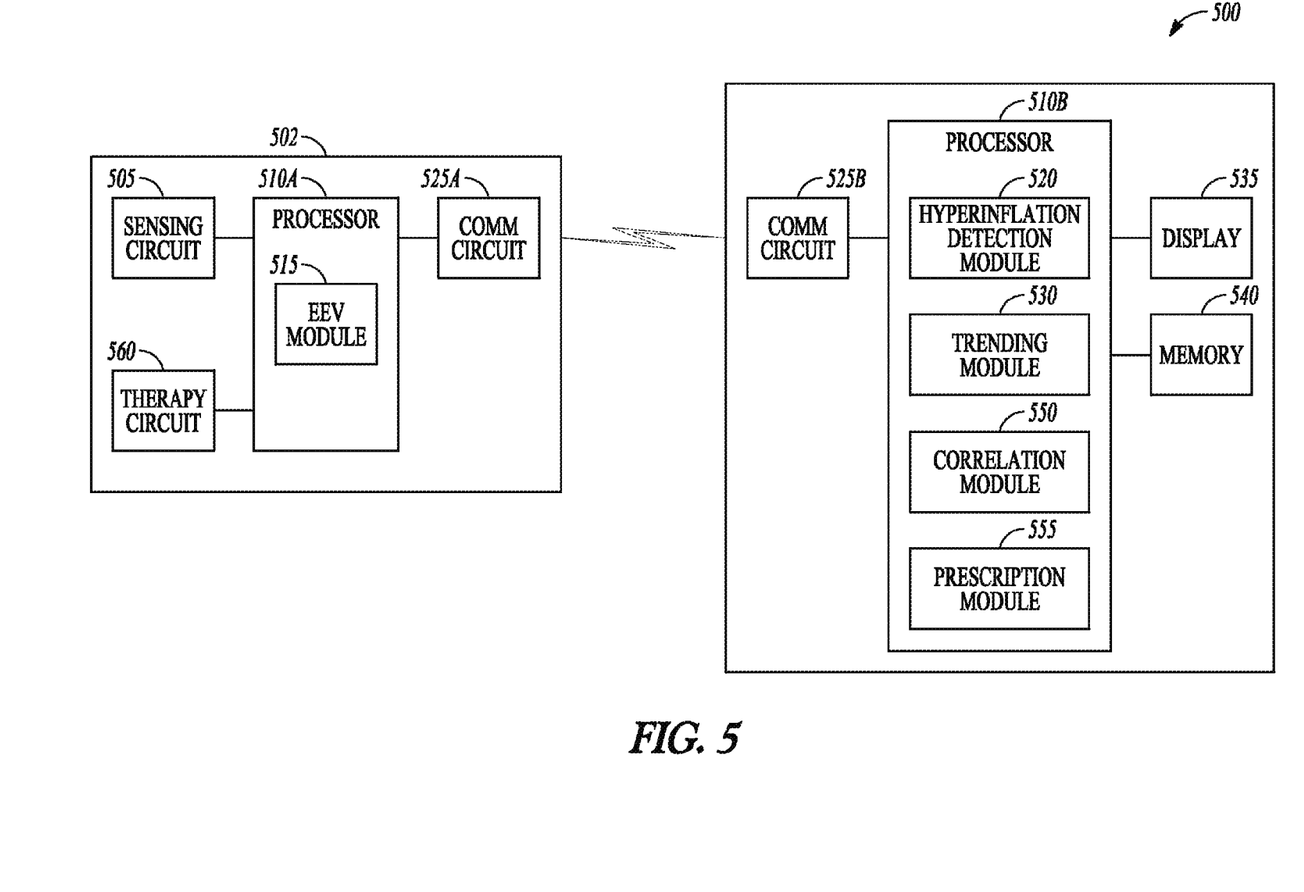
FIG. 5 shows another example of portions of a medical device system to detect lung hyperinflation.

FIG. 5 shows a block diagram of portions of another example of a medical device system 500 to detect lung hyperinflation. The system 500 includes a first medical device 502 and a second medical device 507. The first medical device 502 can be an ambulatory medical device and may be an implantable device, a partially implantable device, or a wearable device. The second device 507 can be an external device and may include an external programmer for programming operational parameters of the first medical device 502 or may include a server located remotely from the first medical device 502.

The first medical device 502 can include a sensing circuit 505, a communication circuit 525A and a first processor 510A. The sensing circuit 505 generates a sensed physiological signal representative of respiration of a subject. Some examples of the sensing circuit 505 include any of the sensing circuits or sensors previously described herein. The communication circuit 525A communicates information with a separate device such as the second medical device 507. The communication circuit 525A may be a wireless communication circuit that communicates via wireless inductive telemetry or far field radio frequency communications. The first processor 510A can include an EEV module 515 that determines a measure representative of EEV of the subject using the physiological signal sensed by the sensing circuit 505.

The second medical device 507 includes a communication circuit 525B that communicates information with the first medical device 502. The second medical device 507 also includes a second processor 510B. The first medical device 502 communicates information, including EEV information, with the second medical device 506. The second processor 510B can include a lung hyperinflation detection module 520 to generate an indication of lung hyperinflation of the subject according to the measure of EEV. The lung hyperinflation detection module 520 may provide the indication to at least one of a user or process.

In some examples, the second medical device 507 may trend values of EEV or a metric of EEV to monitor for worsening episodes of COPD exacerbations. The second processor 510B may include a trending module 530. The trending module 530 may receive the EEV information and trend measured values of EEV or one or more metrics of EEV, such as one or more of EEV magnitude and EEV frequency for example. The second medical device 507 may include a display 535, and the trending module 530 displays the trend of the measure of EEV. In some examples, at least one respiration parameter determined by the EEV module 515 can be communicated from the first medical device 502. Some examples of a respiration parameter include a respiration rate, an inter-breath interval, a measure of variability of respiration rate, a measure of variability of an inter-breath interval, the tidal volume, a measure of variability of tidal volume of the subject, end-expiratory volume (EEV), or a rapid shallow breathing index (RSBI). RSBI may be calculated as (RR/TV). The trending module 530 receives the measure of EEV and the measured respiration parameter, and displays the values of EEV with values of the measured respiration parameter.

A metric of lung hyperinflation may be determined and trended. In some examples, the EEV module 515 measures a respiration parameter of the subject. The respiration parameter may be measured using the same sensed physiological signal used to measure EEV or the respiration parameter may be measured using a second sensed physiological signal representative of respiration of the subject, such as a physiological signal sensed using a different type of sensing circuit from that used to determine EEV.

The trending module 520 may determine a lung hyperinflation index (HII) using the measure of EEV and the measured respiration parameter, trend values of the determined HII of the subject, and display the trend of the determined HII. In some examples, the EEV module 515 measures RR and TV. An example of an HII includes HII=EEV*(RR/TV). In some examples, the EEV module measures relative EEV (rEEV) and relative tidal volume (rTV) and the HII includes HII=rEEV*(RR/rTV). To provide greater detail regarding the mechanisms associated with dynamic lung hyperinflation, the trending module 530 may display plots of one or more of rEEV vs. RSBI, rEEV vs. RR, and rEEV vs. TV.

The second medical device 507 may correlate the lung hyperinflation metric to physical activity level of the subject. For instance, the first medical device 502 may include a sensing circuit that determines a level of physical activity of the subject. The medical device communicates an indication of a level of physical activity of the subject with the value of EEV or the EEV metric. The second medical device may include memory 540 integral to or separate from the processor 510B. The lung hyperinflation detection module 520 may determine the HII using the measure of EEV and the measured respiration parameter, and store values of the HII in association with determined physical activity levels of the subject. The trending module 530 may display a plot of HII vs. physical activity for the subject.

The second medical device 507 may correlate the lung hyperinflation metric to posture of the subject. The first medical device 502 may include a posture sensing circuit to determine posture of the subject. An approach for determining patient posture using a multi-dimensional posture sensor can be found in Wang et al., "Posture Detector Calibration and Use," U.S. Pat. No. 8,366,641, filed Nov. 18, 2005, which is incorporated herein by reference in its entirety. The medical device communicates an indication of posture of the subject with the value of EEV or the EEV metric. The lung hyperinflation detection module 520 may determine the HII using the measure of EEV and the measured respiration parameter, and store values of the HII in association with determined posture of the subject. The trending module 530 may display a plot of HIT vs. posture for the subject.

The second medical device 507 may correlate the calculated lung hyperinflation metric with symptoms of the subject. In some examples, the second medical device 507 includes a port 545 that receives an indication of a symptom into the second medical device 507. The port 545 may be electrically connected to a user interface or the port 545 may be a communication port or COMM Port. The symptom may be an indication of a patient's impression of the severity of the COPD exacerbation or dyspnea (e.g., a severity score). The second processor 510B may include a correlation module 550 that correlates measurements of EEV with the symptom of the subject and display the correlation between the measurements of EEV and the symptom.

In some examples, the second medical device 507 may correlate the calculated lung hyperinflation metric with another diagnosis or other physiologic condition of the subject, such as the subject having HF or that the subject experiences cardiac arrhythmias. The second processor 510B may include a correlation module 550 that correlates measurements of EEV with the other condition or conditions of the subject and display the correlation between the measurements of EEV and the other conditions.

In some examples, the first medical device 502 includes a therapy circuit 560 to control delivery of a therapy to the subject. For instance, the first medical device may be a drug pump and the therapy circuit controls titration of the drug to the subject. The second medical device 507 may initiate delivery of therapy in response to the indication of lung hyperinflation generated by the lung hyperinflation detection module 520.

In some examples, the second medical device 507 can provide a recommendation regarding treatment of the subject. The second processor 510B may include a prescription module 555 that generates a recommendation of therapy for the subject according to the generated indication of lung hyperinflation. For instance, the prescription module 555 may recommend the use of an inhaler for the subject, or may recommend a change to the class of agent used in the inhaler. The recommendation may be provided the indication to at least one of a user (via the display) or process.

In some examples, the second medical device 507 monitors the response of the subject to the treatment. The prescription module 555 may detect an improvement in one or both of the lung hyperinflation index and the respiration parameter. The prescription module 555 may change the recommendation of therapy of the subject back to a previous therapy or a therapy with less negative impact. The prescription module 555 may detect a worsening of the physical condition of the subject. The prescription module 555 may recommend a change to the treatment of the condition of the subject, and may generate an alert to a caregiver or clinician.

Figure 6:
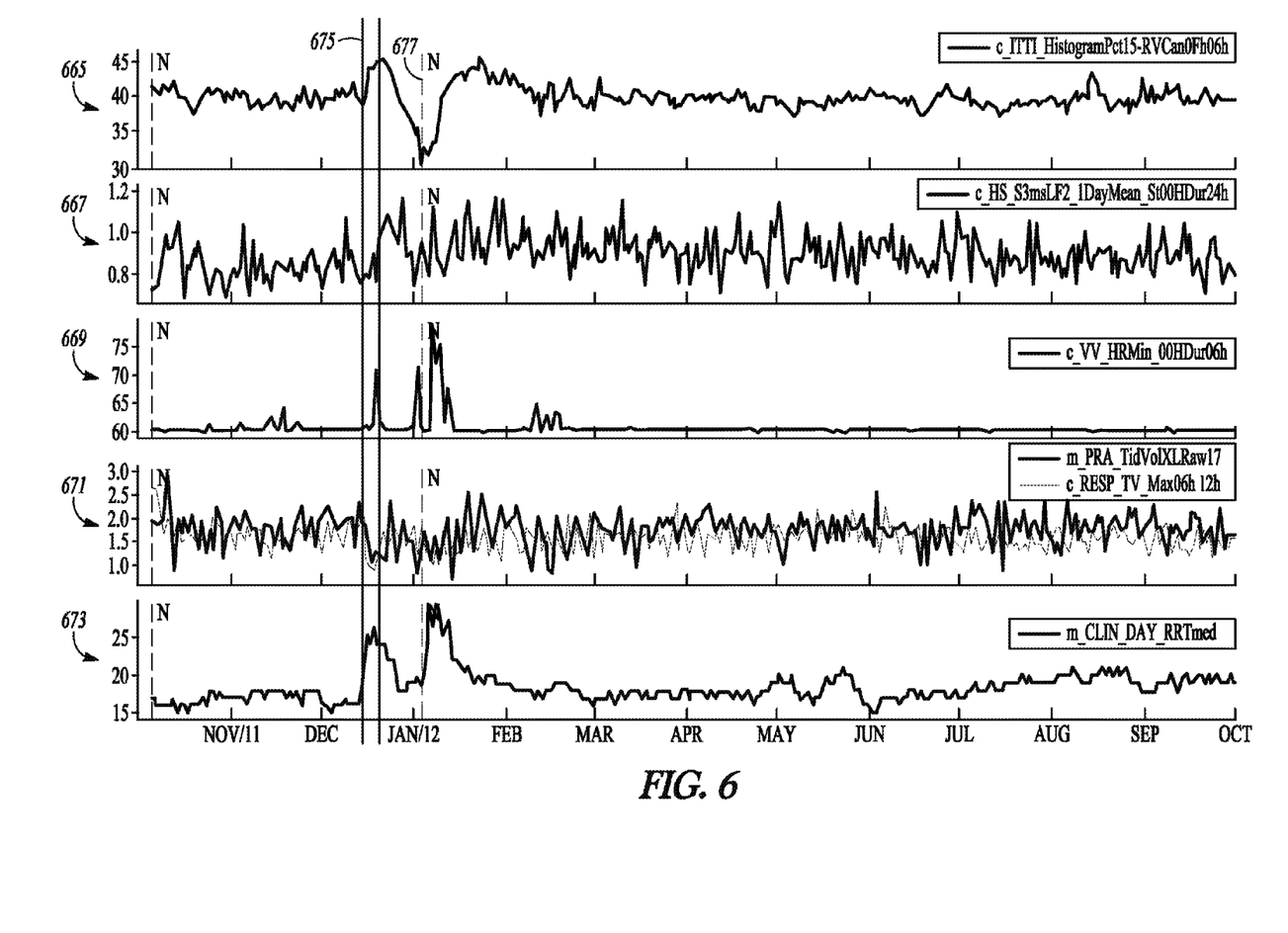
FIG. 6 shows an example of waveforms generated by sensors for an HF patient.

FIG. 6 shows an example of waveforms generated by sensors for an HF patient who developed bronchitis. Although not the same as AECOPD, bronchitis can include some changes to the lungs that occur with AECOPD. The waveforms show trends for thoracic impedance 665, heart sounds 667, heart rate 669, tidal volume 671, and respiratory rate 673. The vertical double lines 675 in the graph correspond to an episode of lung hyperinflation. The waveforms show the onset of lung hyperinflation included increased impedance, increased respiratory rate, and decreased tidal volume. The vertical dashed line 677 shows an episode diagnosed as bronchitis. Inflammation and mucus associated with bronchitis resulted in a decrease in impedance.

The waveforms show that device-based monitoring for lung hyperinflation can lead to early detection and early treatment. The monitoring can lead to immediate treatment if the medical device system is equipped with that capability. Early treatment can reduce the risk of hospitalization for the patient, while prompt medical treatment can prevent worsening conditions and prevent hospitalization of the patient with COPD.

While the examples have been described in regard to detecting lung hyperinflation associated with COPD patients, the examples may be useful to detect other related or unrelated changes in the lung of patients with COPD, other diseases such as asthma, cystic fibrosis, pneumonia, etc., and also including but not limited to changes in airway inflammation, sputum, or cough. The implantable embodiments described may be useful for long-term patient monitoring for disease progression and acute worsening of symptoms (e.g., AECOPD). The wearable embodiments (e.g., a patch device) may be better suited for short-term use such as monitoring patients for the period of time post-discharge from the hospital after being hospitalized for an acute exacerbation of COPD or other cause.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
a first implantable medical device including:
a sensing circuit configured to generate a sensed physiological signal representative of respiration of a subject when operatively coupled to electrodes configured to contact the subject;
a communication circuit configured to communicate information with a separate device; and
a first processor including an end expiratory volume (EEV) module configured to determine a measure representative of EEV of the subject using the sensed physiological signal; and
a second medical device including:
a communication circuit configured to communicate information with the first medical device; and
a second processor including a lung hyperinflation detection module configured to generate an indication of lung hyperinflation of the subject according to the measure of EEV and provide the indication to a user.

2. The system of claim 1, wherein the second device includes a display and the second processor includes a trending module, wherein the trending module is configured to receive values of the measure of EEV, trend the values of the measure of EEV, and display the trend of the measure of EEV with values of a measured respiration parameter of the subject.

3. The system of claim 1,
wherein the EEV module is configured to measure a respiration parameter of the subject using the sensed physiological signal or a second sensed physiological signal representative of respiration of the subject, and
wherein the second medical device includes a display and the second processor includes a trending module, wherein the trending module is configured to determine a lung hyperinflation index (HII) using the measure of EEV and the measured respiration parameter, trend values of the determined HII of the subject, and display the trend of the determined HII.

4. The system of claim 1, wherein the second medical device includes:
a display;
a port configured to receive an indication of a patient symptom into the second medical device; and
wherein the second processor includes a correlation module configured to correlate measurements of EEV with the patient symptom and display the correlation between the measurements of EEV and the patient symptom.

5. The system of claim 1, wherein the wherein the second processor includes a prescription module configured to generate a recommendation of therapy for the subject according to the indication of lung hyperinflation and provide the indication to at least one of a user or process.

6. The system of claim 1, wherein second medical device is configured to initiate delivery of therapy in response to the indication of lung hyperinflation.

7. The system of claim 1,
wherein the first medical device includes a sensing circuit configured to determine a level of physical activity of the subject;
wherein the EEV module is configured to measure a respiration parameter of the subject using the sensed physiological signal or a second sensed physiological signal representative of respiration of the subject, and
wherein the lung hyperinflation detection module is configured to determine a lung hyperinflation index (HII) using the measure of EEV and the measured respiration parameter, and store values of the HII in association with determined physical activity levels of the subject.

8. A method of operating an implantable medical device, the method comprising:
sensing a physiological signal that includes respiration information of a subject using a sensing circuit of the implantable medical device, wherein the sensing circuit produces the physiological signal when operatively coupled to electrodes configured to contact the subject;
determining a value of end expiratory volume (EEV) of the subject using the sensed physiological signal; and
generating, with the implantable medical device, an indication of lung hyperinflation of the subject according to the value of EEV and providing the indication to a user.

9. The method of claim 8, wherein sensing a physiological signal includes sensing a thoracic impedance signal using an implantable sensor of the medical device, and wherein determining a value representative of EEV includes determining a value of EEV using the thoracic impedance signal.

10. An apparatus comprising:
a first physiological sensing circuit configured to generate a first sensed physiological signal, wherein the first sensed physiological signal includes respiration information of a subject;
a processor including:
an end expiratory volume (EEV) module configured to determine a value of EEV of the subject using the first sensed physiological signal; and
a lung hyperinflation detection module configured to generate an indication of lung hyperinflation of the subject according to the value of EEV and provide the indication to a user; and
a second physiological sensing circuit configured to generate a second sensed physiological signal representative of respiration that is separate from the first sensed physiological signal and a physical activity sensing circuit wherein the EEV module is configured to change from determining EEV using the first sensed physiological signal to determining EEV using the second sensed physiological signal when sensed physical activity of the subject exceeds a specified physical activity threshold.

11. The apparatus of claim 10, wherein the first physiological sensing circuit includes a thoracic impedance sensing circuit configured to generate a sensed thoracic impedance signal that varies with breathing of the subject, wherein the EEV module is configured to determine the value of EEV using the thoracic impedance signal.

12. The apparatus of claim 10, wherein the first physiological sensing circuit includes an implantable thoracic impedance sensing circuit, wherein the EEV module is configured to detect an expiration portion of the breathing cycle of the subject using the respiration information, determine a value of thoracic impedance at the end of the expiration portion, and determine the value of EEV using the value of thoracic impedance.

13. The apparatus of claim 10, wherein the first and second physiological sensing circuits each include at least one of a displacement sensing circuit, an acceleration sensing circuit, an airflow sensor, an impedance sensing circuit, and a pressure sensor.

14. The apparatus of claim 10, wherein the EEV module is configured to remove drift in a value of the measure representative of EEV due to non-respiration sources.

15. The apparatus of claim 10, wherein the lung hyperinflation detection circuit is configured to filter measurements of EEV to remove a change in the measurement of EEV contributed by the sensing circuit and preserve a change in the measurement EEV due to lung hyperinflation.

16. The apparatus of claim 10, wherein the first physiological sensing circuit generates a first sensed respiration signal, wherein the second physiological sensing circuit configured to generate a second physiological sensor signal that includes surrogate information of respiration of the subject, wherein the EEV module is configured to determine a measure of EEV using the first sensed respiration signal when both the respiration signal and the second physiological sensor signal indicate respiratory activity.

\* \* \* \* \*